United States Patent [19]

Cousse et al.

[11] 4,006,181

[45] Feb. 1, 1977

[54] PROCESS FOR THE OBTAINING OF ESTERS OF ACETYLSALICYLIC ACID AND AMINO ALCOHOLS

[75] Inventors: Henri Cousse; Gilbert Mouzin, both of Castres, France

[73] Assignee: Pierre Fabre S.A., Paris, France

[22] Filed: Apr. 23, 1975

[21] Appl. No.: 570,760

Related U.S. Application Data

[63] Continuation of Ser. No. 382,400, July 25, 1973, abandoned.

[52] U.S. Cl. .............................................. 260/474
[51] Int. Cl.$^2$ ........................................ C07C 69/84
[58] Field of Search ................................... 260/474

[56] References Cited

UNITED STATES PATENTS 3,468,939  9/1969  Kalterbronn ................... 260/473 F
3,647,859  3/1972  Ogura ............................ 260/474

FOREIGN PATENTS OR APPLICATIONS 2,094,502  1/1972  France .............................. 260/474

Primary Examiner—Paul J. Killos
Attorney, Agent, or Firm—Gordon W. Hueschen

[57] ABSTRACT

The present invention relates to a new process for the obtaining of dimethylaminoethyl acetylsalicylate and its salts.

It is characterized by the fact that the synthesis of the acid chloride is effected in an aliphatic hydrocarbon in the presence of pyridine as catalyst; after condensation with the dimethylaminoethanol, the product obtained is recovered by crystallization in anhydrous medium.

The products obtained can be used in the pharmaceutical industry.

5 Claims, No Drawings

PROCESS FOR THE OBTAINING OF ESTERS OF ACETYLSALICYLIC ACID AND AMINO ALCOHOLS

This is a continuation of application Ser. No. 382,400, filed July 25, 1973, now abandoned.

The present invention (made at the Pierre Fabre Research Center) concerns a new process for the obtaining of N,N-dimethylaminoethyl acetylsalicylate and its salts. These chemical compounds are known for their therapeutic applications (Special Medicament Patent No. 6049 M of Dec. 8, 1966).

In the methods of preparation used up to the present time, the chloride of acetylsalicylic acid was obtained by the action of thionyl chloride, in excess, on acetylsalicylic acid, using benzene as solvent. In accordance with this technique, the acid chloride obtained had to be purified by distillation under a high vacuum. Due to its poor thermal stability, this operation resulted in extensive decomposition and, furthermore, the conditions employed were difficult to extrapolate on an industrial plane. Moreover, the condensation with N-dimethylaminoethanol was effected in the presence of pyridine; as a result, the product obtained at the end of the reaction was N-dimethylaminoethyl acetylsalicylate in the form of of its non-crystallizing free base. The recovery required successive extractions with aqueous solutions of hydrochloric acid and another rectification under vacuum. Finally, it was necessary to salify by means of a solution of hydrochloric acid in anhydrous deperoxidized ether.

The process which forms the object of the present invention is characterized by the fact that the above drawbacks are eliminated. It is possible to avoid the distillation of the acid chloride by preventing the formation of polymers upon the chlorination, namely undesirable products of the formula

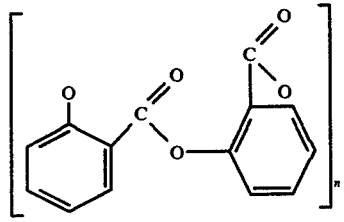

$n = 1, 2 \ldots$

The optimum conditions for the obtaining of the acid chloride in pure state, without distillation, in quantitative yield have been determined. Thus, the formation of the secondary products is considerably decreased when benzene is replaced by hexane or petroleum ether, or chloroform.

Moreover, the preparation of the hydrochloride of N-dimethylaminoethyl acetylsalicylate is effected in the absence of pyridine, using a stoichiometric quantity of DMAE. As a result, the hydrochloric acid formed during the condensation gradually salifies the amine group. The hydrochloride desired is obtained directly and is recovered from the chloroform solution by addition of ether, or ethyl acetate. In this way, one avoids successive washings of the dimethylaminoethyl acetylsalicylate which might result in desacetylation and, therefore, in a very substantial decrease in yield. Moreover, the rectification of the N-dimethylaminoethyl acetylsalicylate is eliminated. Finally, it is no longer necessary to effect the hydrochlorination in anhydrous ether.

This new process is therefore particularly advantageous on an industrial plane since it makes it possible to obtain the desired product while avoiding lengthy, costly operations (rectification, successive washings with aqueous solutions).

The following example illustrates the invention without limiting it.

1. Preparation of acetylsalicylic acid chloride

Acetylsalicylic acid (1,000 g, 5.55 mols) is maintained in suspension in 2 liters of hexane; a catalytic amount of anhydrous pyridine (1 to 3 cc) is added.

The stoichiometric quantity of thionyl chloride is added in portions of the few cc each.

When the addition has been completed, stir for one hour at room temperature and then complete the reaction by heating for 5 hours at 70° C.

The end of the reaction is indicated by the complete dissolving of the acetylsalicylic acid; the kinetics can be observed by checking the liberation of gas or the loss of weight of the reaction mixture.

Concentrate under a slight vacuum; the residual oil obtained crystallizes with a melting point of 49°–50° C. 1,105 g of crystals were recovered, which corresponds to a quantitative yield.

2. Preparation of NN-dimethylaminoethyl acetylsalicylate hydrochloride

To a solution of 456 g (5.1 moles) of dimethylaminoethanol in 3 liters of anhydrous chloroform add, drop by drop, a chloroform solution containing 1,105 g (5.5 moles) of the chloride of acetylsalicylic acid previously obtained. The temperature must be maintained below 50° C during the addition.

Then heat for 6 hours under reflux; the reaction is then complete. This derivative is very unstable in aqueous solution since the velocity of desacetylation of this ester is greater than that of the original acetylsalicylic acid.

The recovery is effected in anhydrous medium by treating the chloroform solution with an equal volume of ethyl ether. The hydrochloride of dimethylaminoethyl acetylsalicylate crystallizes out and can be recovered by filtration.

We obtained 1360 g of white crystals of a melting point of 127° C; yield 93%.

Over-all formula: $C_{13} H_{18} Cl N O_4$

The elementary analysis is in accord with the standards generally required, namely:

% C 54.15; theory: 54.26
% H 6.20; theory: 6.3
% Cl 12.38; theory: 12.32

In infra-red spectrography, presence of characteristic absorption bands $\nu$ C = O at 1730 and 1760 cm$^{-1}$
saline bands from 2500 to 2700 cm$^{-1}$
$\nu$ CH aromatics at 3020 cm$^{-1}$
$\nu$ C = C aromatics at 1610 cm$^{-1}$ The nuclear magnetic resonance spectrum possesses:
a singlet (acetyl) at $\delta = 2.4$ ppm
a singlet (N methyls) at $\delta = 2.9$ ppm.
2 multiplets of methylenes at $\delta = 3.5$ and 4.8 ppm.
a multiplet of aromatic protons centered at $\delta = 7.3$ ppm.

The relative intensity is in agreement with the structure.

3. Obtaining of other salts of NN-dimethylaminoethyl acetylsalicylate

From the chloroform solution of the hydrochloride previously obtained, it is possible to return to the free base by treatment with a resin of the quaternary ammonium type or by bubbling of ammonia.

This base then makes it possible to synthesize the salts with the therapeutically acceptable acids by treating with an acid in stoichiometric quantity. The course of this salification can be followed up on a pH meter.

We claim:

1. A process for preparing the hydrochloride of dimethylaminoethyl acetylsalicylate as a crystallization product comprising treating dimethylaminoethanol in chloroform solution at a temperature below 50° C. during the addition in the absence of pyridine with a stoichiometric amount of the chloride of acetylsalicylic acid and crystallizing the hydrochloride of dimethylaminoethyl acetylsalicylate directly from the reaction mixture.

2. The process of claim 1 wherein the hydrochloride of dimethylaminoethyl acetylsalicylate is converted to the free base by treatment of the chloroform solution of the hydrochloride with a quaternary ammonium resin or by bubbling of ammonia, and the free dimethylaminoethyl acetylsalicylate base is then converted to a therapeutically acceptable acid salt by treatment of the base with a stoichiometric amount of the selected acid.

3. Process according to claim 1, in which the acid chloride is prepared by the action of thionyl chloride in a solvent such as hexane or petroleum ether or chloroform in the presence of pyridine as catalyst.

4. Process according to claim 1, in which the recovery of the hydrochloride of the dimethylaminoethyl acetylsalicylate is effected in anhydrous medium.

5. Process according to claim 4 in which crystallization is effected by the addition of ethyl ether or ethyl acetate to the reaction mixture.

* * * * *

UNITED STATES PATENT OFFICE
CERTIFICATE OF CORRECTION

Patent No. 4,006,181      Dated February 1, 1977

Inventor(s) Henri Cousse, Gilbert Mouzin

It is certified that error appears in the above-identified patent and that said Letters Patent are hereby corrected as shown below:

Please insert the following: ---(30) FOREIGN APPLICATION PRIORITY DATA  July 27, 1972 France 72.27199---

Signed and Sealed this

Thirteenth Day of September 1977

[SEAL]

Attest:

RUTH C. MASON  
Attesting Officer

LUTRELLE F. PARKER  
Acting Commissioner of Patents and Trademarks